United States Patent
Fu et al.

(10) Patent No.: US 10,894,059 B2
(45) Date of Patent: Jan. 19, 2021

(54) NADH COMPOUND COMPOSITION, AND PREPARATION AND USE THEREOF

(71) Applicant: BONTAC BIO-ENGINEERING (SHENZHEN) CO., LTD, Guangdong (CN)

(72) Inventors: Rongzhao Fu, Guangdong (CN); Xieguo Yan, Guangdong (CN); Zhu Dai, Guangdong (CN)

(73) Assignee: BONTAC BIO-ENGINEERING (SHENZHEN) CO., LTD, Guangdong (CN)

( * ) Notice: Subject to any disclaimer, the term of this patent is extended or adjusted under 35 U.S.C. 154(b) by 0 days.

(21) Appl. No.: 16/605,731

(22) PCT Filed: Dec. 22, 2017

(86) PCT No.: PCT/CN2017/118093
§ 371 (c)(1),
(2) Date: Oct. 16, 2019

(87) PCT Pub. No.: WO2019/119445
PCT Pub. Date: Jun. 27, 2019

(65) Prior Publication Data
US 2020/0121709 A1    Apr. 23, 2020

(51) Int. Cl.
*A61K 31/7084*   (2006.01)
*A61K 9/00*   (2006.01)
*A61K 9/20*   (2006.01)
*A61K 31/205*   (2006.01)

(52) U.S. Cl.
CPC ........ *A61K 31/7084* (2013.01); *A61K 9/0053* (2013.01); *A61K 9/2009* (2013.01); *A61K 9/2013* (2013.01); *A61K 9/2018* (2013.01); *A61K 9/2031* (2013.01); *A61K 9/2054* (2013.01); *A61K 9/2068* (2013.01); *A61K 31/205* (2013.01)

(58) Field of Classification Search
None
See application file for complete search history.

(56) References Cited

FOREIGN PATENT DOCUMENTS

| | | |
|---|---|---|
| CN | 1299283 A | 6/2001 |
| CN | 1475211 A | 2/2004 |
| CN | 101011373 A | 8/2007 |
| CN | 101721421 A | 6/2010 |
| CN | 106974933 A | 7/2017 |
| WO | WO-9953921 A1 * | 10/1999 ........... A61K 31/205 |

OTHER PUBLICATIONS

Wan, CN 101011373, Aug. 8, 2007, machine translation. (Year: 2007).*
Takuda, WO 2012011588 A1, Jan. 26, 2012, machine translation. (Year: 2012).*
International Search Report (English and Chinese) and Written Opinion issued in PCT/CN2017/118093, dated Sep. 27, 2018, 11 pages provided.

* cited by examiner

*Primary Examiner* — Layla D Berry
(74) *Attorney, Agent, or Firm* — Hamre, Schumann, Mueller & Larson, P.C.

(57) ABSTRACT

An NADH compound, and a formulation and use thereof, relating to the technical field of biomedicine and health care products. The NADH compound includes NADH or its physiologically acceptable salt and L-carnitine or its physiologically acceptable salt, and can be used as a weight loss product. The NADH compound has an increased effect in weight loss, and may achieve long-term drug administration of the product.

9 Claims, 1 Drawing Sheet

NADH COMPOUND COMPOSITION, AND PREPARATION AND USE THEREOF

CROSS-REFERENCE TO RELATED APPLICATIONS

This application is the national stage of International Application No. PCT/CN2017/118093 filed Dec. 22, 2017, the entire contents of which are incorporated herein by reference.

FIELD OF TECHNOLOGY

The invention relates to the field of biomedicine and health care products, in particular, to new formulations and new uses of NADH in the field of medicine and health care.

BACKGROUND OF THE INVENTION

NADH is an abbreviated form of reduced nicotinamide adenine dinucleotide. Nicotinamide adenine dinucleotide is a physiological substance present in all living cells including human cells, and has no side effects on the body. This substance is a cofactor for many enzymes that catalyze oxidation-reduction reactions and is called coenzyme I.

NADH is generated in the citric acid cycle of glycolysis and respiration in living organisms, acting as a hydrogen donor in the enzymatic reaction. It is involved in many physiological activities such as cellular material metabolism, energy synthesis, and cellular DNA repair, and is a control marker in the energy production chain of mitochondria. The most important role of NADH is to act as the driving force for cellular respiration. ATP produced by direct metabolism through glucose metabolism is very small. However, the metabolically produced NADH can produce a large amount of ATP via an electron-transfer oxidative phosphoric acid reaction, thereby meeting the energy needs of the organism.

NADH is widely used in chemical catalytic reactions, API production, health care products, and cosmetics. Reports on the application of NADH in the field of medicine and health care products have been widely reported, for example, for anti-aging, prevention and treatment of chronic diseases, but no reports on the use of NADH for weight loss have been given.

According to statistics from WHO, more than 1.4 billion adults over the age of 20 are overweight; among overweight adults, more than 200 million men and nearly 300 million women are obese. All in all, more than 10% of global adults are obese. In addition, 44% of the burden of diabetes, 23% of the burden of ischemic heart disease, and 7% to 41% of the burden of certain cancer can be attributed to overweight and obesity. According to statistics, at least 2.8 million adults die each year from overweight or obesity. Overweight and obesity are now the fifth biggest risk leading to death worldwide.

In 2016, the famous British medical magazine Lancet published a report on the global adult weight survey, showing that the obesity population for global adult has surpassed that for the thinner, and China has surpassed the United States to become the country with the most obese population in the world. Among which, the number of obese men in China is 43.2 million, and the number of obese women is 46.4 million. The absolute number of obese people in China has reached the highest in the world.

For the overweight and obesity, although a large number of research and development forces have been invested at home and abroad, there are only a handful of drugs targeting at weight loss approved by the Food and Drug Administration due to the difficulty in research and development. But these drugs still have the following two problems: 1. Drug administration is associated with weight-related diseases such as hypertension, type 2 diabetes or hyperlipidemia; 2. Long-term use of these drugs may cause different levels of side effects such as headache, dizziness, fatigue, nausea and dry mouth, and there will be a relapse after stopping the drug.

With the popularization of the concept of healthy green life, more and more people are eager for natural slimming products, especially those with L-carnitine. L-carnitine is popular among people because it is derived from red meat such as beef and pork, and has no toxic side effects on human body.

L-carnitine, also called L-carnitine, L-carnitine, vitamin BT, or carnitine by translation through pronouciation. Its chemical name is β-hydroxy γ-trimethylammonium butyrate, which is an amino acid that promotes the conversion of fat into energy. As a weight loss product, L-carnitine mainly characterized by (1) only reducing fat without reducing moisture, (2) doubling the effect of exercise in losing weight, and (3) being the safest and healthiest weight loss supplement. At present, L-carnitine has been applied in the fields of medicine, health care products and food, and has been prescribed as a multi-purpose nutrient by Switzerland, France, the United States and the World Health Organization. Standards for uses of food additives GB2960-1999 in China stipulates that L-carnitine tartrate is a food nutrition enhancer, which can be applied to chewable tablets, soft drinks, capsules, milk powder and milk drinks.

The role of L-carnitine in fat metabolism has been confirmed, which plays the role of "fat transporter". Specifically, the place where fat is oxidized and decomposed is in the mitochondria. If fat does not enter the mitochondria, no matter how the exercise or the diet is, it cannot be consumed. To enter the mitochondria, the fat must first break through the mitochondrial membrane, and breaking through this barrier must depend on the transport function of the carrier L-carnitine. If the fat is compared to coal, and the mitochondria is compared to a boiler, the L-carnitine is equivalent to a shovel, which feeds coal (fat) into the boiler (mitochondria) for combustion.

People usually take less than 50 mg of L-carnitine from their diet every day. However, in order to achieve the desired state of health, ordinary adults should consume no less than 500 mg of L-carnitine per day. Obese people and vegetarians, especially women, need more. Therefore, L-carnitine should be supplemented in addition to the meal to meet the requirements for maintaining an ideal body. However, the study has found that although people take L-carnitine for weight loss as much as 1~3 g, there is no obvious increase in L-carnitine content in muscle, which cannot maximize the effect of the product, resulting in the absolute bioavailability of L-carnitine being only 15.9±4.9% and hence reduced effect in weight loss effect.

SUMMARY OF THE INVENTION

For the technical problem of low bioavailability and reduced effect in weight loss for the L-carnitine weight loss products currently on the market mentioned in the above background art, the purpose of the present invention is to develop a new use of NADH in weight loss, in order to obtain a new weight loss product, so as to solve the above-mentioned deficiencies of L-carnitine weight loss products.

To achieve the above purpose, the inventor has conducted a long-term and extensive experimental study. The metabolic process of fat includes the following two stages: the first stage: fatty acids are transported from the outside of mitochondria to the inside of mitochondria by L-carnitine; the second stage: fatty acids undergo beta-oxidative decomposition in the mitochondria to produce energy. The inventor has found that the second stage of fat metabolism requires the participation of coenzyme NADH, which hinders the metabolism of fat when NADH is deficient in the body. Taking L-carnitine and enhancing exercise may actually introduce more fatty acids into the mitochondria for oxidation, and the human body may also self-regulate to produce more NADH to accelerate oxidation. However, the above is not enough to lose enough fat, because the synthesis of NADH in the body will not increase much in a short time. In this way, the fatty acids transported into the mitochondria may not be caused to be consumed in a timely manner, thereby inhibiting the fatty acid from being again transported to the mitochondria; then the human body will self-regulate and metabolize excess L-carnitine. This is why a lot of L-carnitine is taken but no significant increase in L-carnitine is found in the muscle.

Based on the above study by the inventor, the present invention provides an NADH compound composition comprising the following components in parts by weight: an NADH or a physiologically acceptable salt thereof; and an L-carnitine or a physiologically acceptable salt thereof. The physiologically acceptable salt of NADH and L-carnitine includes all known physiologically acceptable acidic and basic salt forming substances, of which an NADH sodium salt and a L-carnitine tartrate are more preferred.

Preferably, the composition comprises the following components in parts by weight: 1 to 10% of an NADH or a physiologically acceptable salt thereof, 1 to 10% of an L-carnitine or a physiologically acceptable salt thereof, 5~50% of an oil phase, 20~70% of an emulsifier, and 0~50% of a co-emulsifier.

Preferably, the oil phase is selected from at least one of soybean oil, ethyl oleate, isopropyl myristate, isopropyl palmitate, corn oil, castor oil, caprylic/capric triglyceride, glycerol monooleate, oleic acid, olive oil, sesame oil, peanut oil and almond oil.

Preferably, the emulsifier is a nonionic surfactant.

More preferably, the emulsifier is selected from at least of polyoxyethylene castor oil, polyoxyethylene hydrogenated castor oil, polyethylene glycol stearate-15, oleic acid polyethylene glycol glyceride, polyethylene glycol octyl phenyl ether, octanoic acid decanoic acid polyethylene glycol glyceride, polosham 188, tween-80, liquid lecithin, sucrose laurate, sucrose palmitate, sucrose stearate, polyethylene glycol glyceride and glycerol polyethylene glycol-75-stearate.

Preferably, the co-emulsifier is selected from at least one of ethanol, propylene glycol, polyethylene glycol 200, polyethylene glycol 400, and isopropanol, 1,2-propanediol, n-butanol, diethylene glycol monoethyl ether and propylene carbonate.

Preferably, the above NADH compound composition is prepared by a preparation method comprising the steps of: weighing a prescribed amount of an oil phase, an emulsifier and a co-emulsifier in a vial, and adding a prescribed amount of an NADH or a physiologically acceptable salt thereof for mixing uniformly to obtain a clear liquid; further adding a prescribed amount of an L-carnitine or a physiologically acceptable salt thereof for fully stirring at 37° C. for 1 hour to be completely dissolved, thereby obtaining the product. The NADH compound composition may be directly filled in a soft capsule for oral administration, or may be dispersed in a pharmaceutical excipient such as a carrier material, compressed into a tablet for use, or added with a sustained-release material to prepare a sustained-release preparation.

The present invention further provides an NADH compound oral preparation comprising the above NADH compound composition provided by the present invention, and the oral preparation is preferably a tablet preparation or a capsule preparation.

Preferably, in addition to the above NADH compound composition, the oral preparation further comprises a pharmaceutical excipient, and the pharmaceutical excipient comprises the following components in parts by weight: 10~70% of an adsorbent, 10~80% of a thinner, 0~10% of an adhesive, 5~10% of a disintegrator, 0~3% of a flavoring agent and 0.5~4% of a lubricant; a weight ratio of the pharmaceutical excipient to the NADH compound composition is 20:1~5:2.

Preferably, the adsorbent is selected from at least one of anhydrous calcium chloride, calcium phosphate, calcium carbonate, magnesium carbonate, magnesium oxide microsilica, microcrystalline cellulose, lactose, aluminum hydroxide gel powder, sodium chloride, pregelatinized starch, sucrose powder, glucose powder, mannitol, sorbitol starch, cyclodextrin, sodium carbonate, sodium bicarbonate, calcium sulfate, povidone, polyethylene glycol 4000 and polyethylene glycol 6000.

Preferably, the thinner is selected from at least one of microcrystalline cellulose, calcium hydrogen phosphate, lactose, starch, dextrin, mannitol, glucose powder, sucrose powder, and sorbitol.

Preferably, the adhesive is selected from at least one of polyvinylpyrrolidone, hydroxypropylmethylcellulose, hydroxypropylcellulose, various concentrations of ethanol solution, and water.

Preferably, the disintegrator is selected from at least one of cross-linked carboxymethylcellulose sodium, cross-linked polyvinylpyrrolidone, sodium carboxymethyl starch, low-substituted hydroxypropylcellulose and partially pregelatinized starch.

Preferably, the flavoring agent is selected from at least one of stevioside, aspartame, citric acid, food flavor, lactose, glucose, sucrose and mannitol.

Preferably, the lubricant is selected from at least one of micronized silica gel, magnesium stearate, talc and sodium stearyl fumarate.

Preferably, the above NADH compound oral preparation may be prepared by the method according to any one of the following 1 to 3:

1. Weighing the above NADH compound composition and various pharmaceutical excipients according to the ratio, adding a soft material made of a diluent, a binder, a flavoring agent and a partial disintegrating agent after the NADH compound composition is adsorbed by the adsorbent for sieving the granules by 18 mesh or 20 mesh sieve and drying to obtain dry granules; then sieving the dry granules with 18 mesh or 20 mesh sieve, adding a lubricant and the remaining disintegrant for mixing and evenly compressing, to obtain an NADH compound oral tablet preparation;

2. Weighing the above NADH compound composition and various pharmaceutical excipients according to the ratio, uniformly mixing with the other pharmaceutical excipients after the NADH compound composition is adsorbed by the adsorbent, and directly compressing, to obtain an NADH compound oral tablet preparation;

3. Weighing the above NADH compound composition and various pharmaceutical excipients according to the ratio, adding a soft material made of other pharmaceutical excipients after the NADH compound composition is adsorbed by the adsorbent for sieving the granules by 18 mesh or 20 mesh sieve and drying to obtain dry granules, then sieving the dry granules with 14 mesh or 18 mesh sieve, filling the whole granules in a capsule shell, to obtain an NADH compound oral capsule preparation.

The present invention further provides a new use of NADH in the field of medicine and health products, that is, a use of the above NADH compound composition containing the NADH as a main component or the above NADH compound oral preparation in the preparation of a slimming product.

The present invention further provides a slimming method, specifically, comprising steps of administering a physiologically acceptable amount of the above NADH compound composition or a physiologically acceptable amount of the above NADH compound oral preparation to the slimmer.

Beneficial Effects:

Compared with the prior art, the present invention has the following advantages:

1. The present invention combines NADH with L-carnitine for the first time to provide a new slimming product, which compensates for the lack of L-carnitine bioavailability due to lack of NADH during the simple addition of L-carnitine in the process of fat metabolism, and has an increased effect in weight loss as compared with the existing simple L-carnitine weight loss products.

2. The NADH compound composition composed of the active ingredient, the oil phase, the emulsifier and the co-emulsifier provided by the present invention may spontaneously emulsify in the body to form tiny emulsion droplets with a particle size ranging from 10 to 100 nm after oral administration, which greatly increases the contact area of the drug with the medium and the mucosa, promotes the oral absorption of the drug, further enhances the effect in weight loss, and improves the bioavailability of L-carnitine.

3. The NADH compound composition provided by the present invention is a thermodynamically stable uniform system, which significantly improves the stability of NADH and L-carnitine, and may achieve long-term drug administration of the product.

4. The preparation process for the NADH compound composition and the preparation thereof provided by the present invention is simple and easy without special instrument or equipment, having advantages of low cost, energy saving and environmental protection.

DESCRIPTION OF THE EMBODIMENTS

Figure 1:
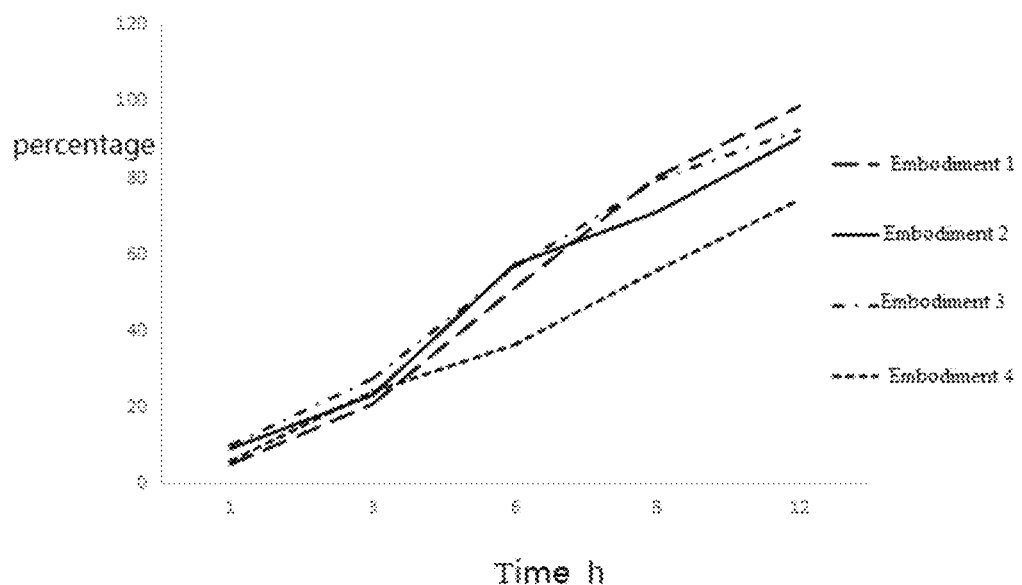
FIG. 1 is an in vitro cumulative release profile of a NADH compound oral tablet preparation provided by the present invention, wherein the abscissa is the release time (h) and the ordinate is the cumulative release percentage (%)

The present invention will be further described in detail below with reference to the specific embodiments and the accompanying drawings. The following examples are illustrative of the invention, and the present invention is not limited to the following examples.

The raw materials and chemical reagents used in the following embodiments are all commercially available.

Embodiment 1

1. The Formula of NADH Compound Oral Tablet Preparation is as Follows:

| | |
|---|---|
| NADH | 5 g |
| L-carnitine | 5 g |
| Soybean oil | 22 g |
| Polyoxyethylene castor oil | 40 g |
| Lactose | 25 g |
| Microcrystalline cellulose PH101 | 100 g |
| Calcium hydrogen phosphate | 80 g |
| Hydroxypropylmethylcellulose | 12 g |
| Low substituted hydroxypropyl cellulose | 30 g |
| Stevioside | 3 g |
| Sodium stearyl fumarate | 10 g |
| Total | 1000 tablet/granule |

2. The Preparation Method is as Follows:

Each component is weighed according to the above formula, and soybean oil, polyoxyethylene castor oil and NADH are added into a vial for mixing uniformly to obtain a clear liquid; then L-carnitine is added for thoroughly stirring at 37° C. for 1 hour to be completely dissolved, thereby obtaining an NADH compound composition solution.

Next, the NADH compound composition solution is adsorbed with lactose, and after the adsorption is complete, microcrystalline cellulose PH101, calcium hydrogen phosphate, stevioside, hydroxypropylmethylcellulose and ¾ amount of low-substituted hydroxypropylcellulose are added for mixing uniformly by 20 mesh to prepare granules, then drying for sieving again by 18 mesh to prepare the whole granules. The obtained granules may be filled in a DRcaps acid-resistant capsule to obtain a NADH compound oral capsule preparation; or sodium stearyl fumarate and the remaining low-substituted hydroxypropyl cellulose are added for mixing uniformly and compressing to obtain the NADH compound oral tablet preparation.

3. Determination for Disintegration 6 pieces of the prepared NADH compound oral tablet preparation are taken in a 250 ml beaker, and gently shaken by adding 100 ml of water at 20±1° C., for recording a time through the No. 2 screen, which is 68±2 s. The obtained suspension is filtered through a 0.45 μm microporous membrane to remove insoluble solid adjuvant, and the particle size is determined to be 32±3 nm.

Embodiment 2

1. The Formula of NADH Compound Oral Tablet Preparation is as Follows:

| | |
|---|---|
| NADH | 8 g |
| L-carnitine | 4 g |
| Ethyl oleate | 20 g |
| Polyoxyethylene hydrogenated castor oil | 35 g |
| Diethylene glycol monoethyl ether | 15 g |
| Anhydrous calcium chloride | 20 g |
| Microcrystalline cellulose PH101 | 120 g |
| Polyvinylpyrrolidone | 5 g |
| Croscone sodium | 25 g |
| Aspartan | 3 g |
| Microsilica gel | 10 g |
| Magnesium stearate | 2 g |
| Total | 1000 tablet/granule |

2. The Preparation Method is as Follows:

Each component is weighed according to the above formula, and ethyl oleate, polyoxyethylene hydrogenated castor oil, diethylene glycol monoethyl ether and NADH are added into a vial for mixing uniformly to obtain a clear liquid; then L-carnitine is added for thoroughly stirring at 37° C. for 1 hour to be completely dissolved, thereby obtaining an NADH compound composition solution.

Next, the NADH compound composition solution is adsorbed with anhydrous calcium chloride, and after the adsorption is complete, microcrystalline cellulose PH101, aspartame, polyvinylpyrrolidone and ½ amount of croscarmellose sodium are added for mixing uniformly and sieving by 20 meshes to prepare granules, then drying for sieving again by 18 meshes to prepare the whole granules. The obtained granules may be filled in a DRcaps acid-resistant capsule to obtain a NADH compound oral capsule preparation; or magnesium stearate and remaining croscarmellose sodium are added for mixing uniformly and compressing to obtain the NADH compound oral tablet preparation.

3. Determination for Disintegration 6 pieces of the prepared NADH compound oral tablet preparation are taken in a 250 ml beaker, and gently shaken by adding 100 ml of water at 20±1° C., for recording a time through the No. 2 screen, which is 70±2 s. The obtained suspension is filtered through a 0.45 μm microporous membrane to remove insoluble solid adjuvant, and the particle size is determined to be 30±3 nm.

Embodiment 3

1. The formula of NADH compound oral tablet preparation is as follows:

| | |
|---|---|
| NADH sodium salt | 3 g |
| L-carnitine tartrate | 7 g |
| Isopropyl myristate | 15 g |
| Isopropyl palmitate | 15 g |
| Polyoxyethylene castor oil | 15 g |
| Pregelatinized starch | 25 g |
| Lactose | 70 g |
| Microcrystalline cellulose PH102 | 130 g |
| 70% ethanol | 30 g |
| Low substituted hydroxypropyl cellulose | 30 g |
| Stevioside | 3 g |
| Food flavor | 1 g |
| Sodium stearyl fumarate | 10 g |
| Total | 1000 tablet/granule |

2. The preparation method is as follows:

Each component is weighed according to the above formula, and isopropyl myristate, isopropyl palmitate, polyoxyethylene castor oil and NADH are added into a vial for mixing uniformly to obtain a clear liquid; then L-carnitine is added for thoroughly stirring at 37° C. for 1 hour to be completely dissolved, thereby obtaining an NADH compound composition solution.

Next, the NADH compound composition solution is adsorbed with pregelatinized starch, and after the adsorption is complete, lactose, microcrystalline cellulose PH102, stevioside, food flavor, 70% ethanol and ½ amount of low-substituted hydroxypropyl cellulose are added for mixing uniformly and sieving by 18 mesh to prepare granules, then drying for sieving again by 18 mesh to prepare the whole granules. The obtained granules may be filled in a DRcaps acid-resistant capsule to obtain a NADH compound oral capsule preparation; or sodium stearyl fumarate and the remaining low-substituted hydroxypropyl cellulose are added for mixing uniformly and compressing to obtain the NADH compound oral tablet preparation.

3. Determination for Disintegration 6 pieces of the prepared NADH compound oral tablet preparation are taken in a 250 ml beaker, and gently shaken by adding 100 ml of water at 20±1° C., for recording a time through the No. 2 screen, which is 65±2 s. The obtained suspension is filtered through a 0.45 μm microporous membrane to remove insoluble solid adjuvant, and the particle size is determined to be 27±3 nm.

Embodiment 4

1. The Formula of NADH Compound Oral Tablet Preparation is as Follows:

| | |
|---|---|
| NADH | 10 g |
| L-carnitine | 10 g |
| Isopropyl myristate | 30 g |
| Polyoxyethylene castor oil | 15 g |
| Lactose | 110 g |
| Microcrystalline cellulose | 110 g |
| 70% ethanol | 20 g |
| Crosslinked polyvinylpyrrolidone | 30 g |
| Aspartan | 3 g |
| Food flavor | 2 g |
| Magnesium stearate | 10 g |
| Total | 1000 tablet/granule |

2. The Preparation Method is as Follows:

Each component is weighed according to the above formula, and isopropyl myristate, polyoxyethylene castor oil and NADH are added into a vial for mixing uniformly to obtain a clear liquid; then L-carnitine is added for thoroughly stirring at 37° C. for 1 hour to be completely dissolved, thereby obtaining an NADH compound composition solution.

Next, the NADH compound composition solution is adsorbed with lactose, and after the adsorption is complete, microcrystalline cellulose, aspartame, food flavor, 70% ethanol and ½ amount of cross-linked polyvinylpyrrolidone are added for mixing uniformly and sieving by 18 meshes to prepare granules, then drying for sieving again by 18 meshes to prepare the whole granules. The obtained granules may be filled in a DRcaps acid-resistant capsule to obtain a NADH compound oral capsule preparation; or magnesium stearate and remaining crosslinked polyvinylpyrrolidone are added for mixing uniformly and compressing to obtain the NADH compound oral tablet preparation.

3. Determination for Disintegration 6 pieces of the prepared NADH compound oral tablet preparation are taken in a 250 ml beaker, and gently shaken by adding 100 ml of water at 20±1° C., for recording a time through the No. 2 screen, which is 57±2 s. The obtained suspension is filtered through a 0.42 µm microporous membrane to remove insoluble solid adjuvant, and the particle size is determined to be 25±1 nm.

Embodiment 5

Comparative Experimental Study on Pharmacological Evaluation of Mice

Test Subject:

Fifty male mice are selected at 6 weeks of age. The basal feed is fed for two weeks before the start of the experiment, and the initial body weight is 26±2 g.

Grouping:

All experimental groups are randomly divided into 5 groups of 10 each, and the groups were as follows.

① obesity experiment group: 1 group; ② obesity experiment group: 2 groups; ③ obese control group;

④ obese blank group; ⑤ normal blank group

Mouse Model Establishment:

Cage feeding, 5 in 1 cage; ambient temperature of 22±2° C., humidity of 45~65%; the light illumination alternates for 12 h, and the mice are free to eat and drink. Among them, the normal blank group is fed with normal feed, and the other 4 groups are fed with high fat feed; changes in body weight are recorded twice a week; the feeding process lasts 6 weeks to establish the model.

Administration Method:

Group ① is given a solution of the NADH compound composition prepared in Embodiment 1 by gavage once a day;

Group ② is given a mixture of NADH and L-carnitine in Embodiment 1 (without other ingredients) by gavage once a day;

Group ③ is given L-carnitine by gavage once a day;

the amount of administration for Group ①, Group ② and Group ③ is 50 mg according to L-carnitine;

during the period, 5 groups of mice are fed with normal diet in free diet, and continued to be observed for 4 weeks.

Experimental Results:

At the end of the experiment, the mice are weighed and the mice are dissected, then the fat and liver around the kidney and around the testicles are weighed to calculate the average body weight growth rate of each group of mice (weight growth rate %=weight growth/experimental initial weight*100) and average body fat ratio (body fat ratio %=(fat weight around the kidney+fat weight around the testicles)/body weight after test*100). The experimental results are shown in Table 1.

TABLE 1

| Groups | ① | ② | ③ | ④ | ⑤ |
|---|---|---|---|---|---|
| Number of mice | 10 | 10 | 10 | 10 | 10 |
| Body weight growth rate (%) | 38.00 ± 1.98 | 42.08 ± 1.04 | 44.98 ± 3.44 | 58.01 ± 3.00 | 32.19 ± 0.53 |
| Body fat ratio (%) | 2.01 ± 0.33 | 1.98 ± 0.74 | 2.35 ± 2.69 | 2.99 ± 0.47 | 1.85 ± 1.58 |

Embodiment 6

Detection for in Vitro Release

The NADH compound oral tablet preparations prepared in Embodiments 1 to 4 are respectively taken for sampling at 1 hour, 3 hours, 6 hours, 8 hours, 12 hours at 100 rpm in an acidic release medium at 37±0.1° C., pH 1.0; then the cumulative release percentage is calculated by high performance liquid chromatography, and a release profile is plotted in FIG. 1, wherein the release time (h) is plotted on the abscissa, and the cumulative release percentage (%) is plotted on the ordinate..

Embodiment 7

Electron Microscopy

Figure 2:
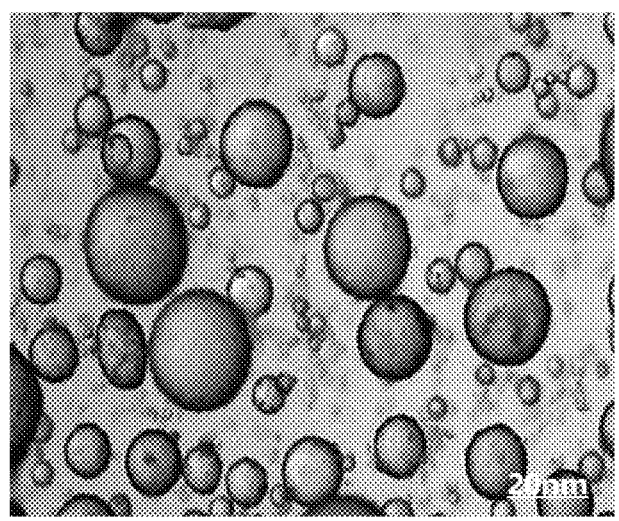
FIG. 2 is an electron micrograph of a NADH compound oral tablet preparation provided by the present invention.

The NADH compound oral tablet preparation prepared in Embodiment 1 is placed in 100 mL of purified water and stirred with a glass rod for 5 minutes; then, the supernatant is centrifuged at 5000 rpm to obtain a supernatant having an opalescence, which is examined by electron microscopy, and an electron micrograph is shown in FIG. 2.

Embodiment 8

Comparison in Stability

The NADH compound oral tablet preparation prepared in Embodiment 1 and the commercially available ENADA® product are placed at 40° C. and 75% humidity for examining the stability, and sampling of the experimental samples are performed at 0, 1, 2, and 3 months, respectively, the experimental results being shown in Table 2.

TABLE 2

| | Detection time (M) | | | | | | | |
|---|---|---|---|---|---|---|---|---|
| | 0 | | 1 | | 2 | | 3 | |
| Detection subject | Maximum impurity (%) | Total impurity (%) | Maximum impurity (%) | Total impurity (%) | Maximum impurity (%) | Total impurity (%) | Maximum impurity (%) | Total impurity (%) |
| Embodiment 1 | 0.01 | 0.01 | 0.04 | 0.09 | 0.09 | 0.13 | 0.11 | 0.15 |
| ENADA | 0.05 | 0.07 | 0.11 | 0.23 | 0.31 | 1.02 | 0.89 | 1.53 |

What is claimed is:

1. A human body slimming method via body exercise, comprising: administering an obese person a physiologically acceptable amount of a slimming product comprising: an NADH or a physiologically acceptable salt thereof; and an L-carnitine or a physiologically acceptable salt thereof.

2. The human body slimming method of claim 1, the slimming product is an oral preparation in the form of a tablet or a capsule.

3. The human body slimming method according to claim 2, wherein the slimming product comprises the following components in parts by weight: 1 to 10% of the NADH or physiologically acceptable salt thereof, 1 to 10% of the L-carnitine or physiologically acceptable salt thereof, 5~50% of an oil phase, 20~70% of an emulsifier, and 0~50% of a co-emulsifier.

4. The human body slimming method according to claim 3, wherein the slimming product is prepared by a preparation method comprising:
   mixing the oil phase, the emulsifier, the co-emulsifier, and adding the NADH or the physiologically acceptable salt thereof to obtain a clear liquid; and
   adding the L-carnitine or the physiologically acceptable salt thereof into the clear liquid and stirring at 37° C. for 1 hour to be dissolved.

5. The human body slimming method according to claim 3, wherein the slimming product further comprises a pharmaceutical excipient,
   the pharmaceutical excipient includes the following components in parts by weight: 10~70% of an adsorbent, 10~80% of a thinner, 0~10% of an adhesive, 5~10% of a disintegrator, 0~3% of a flavoring agent, and 0.5~4% of a lubricant, and
   a weight ratio of the pharmaceutical excipient to the slimming product is 20:1~5:2.

6. The human body slimming method of claim 1, wherein the slimming product further comprises soybean oil, polyoxyethylene hydrogenated castor oil, lactose, microcrystalline cellulose, calcium hydrogen phosphate, and stevioside.

7. The human body slimming method of claim 1, wherein the slimming product further comprises ethyl oleate, polyoxyethylene hydrogenated castor, diethylene glycol monoethyl ether, calcium chloride, cellulose, polyvinylpyrrolidone, croscone sodium, aspartan, mircosilica gel, and magnesium stearate.

8. The human body slimming method of claim 1, wherein the slimming product further comprises isopropyl myristate, isopropyl palmitate, polyoxyethylene castor oil, pregelatinized starch, lactose, cellulose, stevioside, food flavor, and sodium stearyl fumarate.

9. The human body slimming method of claim 1, wherein the slimming product further comprises isopropyl myristate, polyoxyethylene castor oil, lactose, cellulose, crosslinked polyvinylpyrrolidone, aspartan, food flavor, and magnesium stearate.

* * * * *